United States Patent
Seo et al.

(10) Patent No.: US 12,054,770 B2
(45) Date of Patent: Aug. 6, 2024

(54) APPARATUS AND METHOD FOR PCR DIAGNOSIS BASED ON MULTI-WAVELENGTH LIGHT SOURCE

(71) Applicant: ELECTRONICS AND TELECOMMUNICATIONS RESEARCH INSTITUTE, Daejeon (KR)

(72) Inventors: Hong-Seok Seo, Daejeon (KR); Won Kyoung Lee, Daejeon (KR); Jeong Won Park, Seoul (KR); Chul Huh, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 268 days.

(21) Appl. No.: 17/369,598

(22) Filed: Jul. 7, 2021

(65) Prior Publication Data
US 2022/0064702 A1 Mar. 3, 2022

(30) Foreign Application Priority Data

Aug. 26, 2020 (KR) ........................ 10-2020-0107610
Dec. 30, 2020 (KR) ........................ 10-2020-0187926

(51) Int. Cl.
*C12Q 1/686* (2018.01)
*C12Q 1/6818* (2018.01)
(Continued)

(52) U.S. Cl.
CPC ........... *C12Q 1/686* (2013.01); *C12Q 1/6818* (2013.01); *G01N 21/6486* (2013.01); *G01N 33/54373* (2013.01)

(58) Field of Classification Search
CPC .................. C12Q 1/686; C12Q 1/6818; C12Q 2563/107; C12Q 2565/101;
(Continued)

(56) References Cited

U.S. PATENT DOCUMENTS 6,369,893 B1 * 4/2002 Christel ............. G01N 21/0332
356/417
8,137,616 B2 3/2012 Sagner et al.
(Continued)

FOREIGN PATENT DOCUMENTS

JP 4917883 B2 4/2012
KR 10-2015-0130453 A 11/2015
(Continued)

OTHER PUBLICATIONS

D'Andrea, et al, "The study of polyplex formation and stability by time-resolved fluorescence spectroscopy of SYBR Green I-stained DNA", Photochem. Photobiol. Sci., 2014, 13, 1680-1689.
(Continued)

*Primary Examiner* — Young J Kim (57) ABSTRACT

An apparatus for a polymerase chain reaction (PCR) diagnosis includes a transmitter that includes a multi-wavelength light source outputting a first light source signal and a second light source signal, which have different wavelengths, and that applies the first light source signal and the second light source signal to a DNA sample, a code generator that generates a first code signal and a second code signal corresponding to the first light source signal and the second light source signal, respectively, a delay controller that generates a first delay signal and a second delay signal corresponding to the first code signal and the second code signal, respectively, and a receiver that compares the first and second fluorescent signals emitted from the DNA sample with the first and second delay signals, and accu-
(Continued)

mulatively integrates the first fluorescent signal or the second fluorescent signal based on the comparison result.

10 Claims, 5 Drawing Sheets

(51) Int. Cl.
*G01N 21/64* (2006.01)
*G01N 33/543* (2006.01)

(58) Field of Classification Search
CPC ......... C12Q 2537/165; G01N 21/6486; G01N 33/54373; G01N 2021/6484; G01N 21/6408
See application file for complete search history.

(56) References Cited

U.S. PATENT DOCUMENTS

| | | |
|---|---|---|
| 10,138,513 B2 | 11/2018 | Chung et al. |
| 10,386,290 B2 | 8/2019 | Kaduchak et al. |
| 11,504,717 B2 | 11/2022 | Gutekunst et al. |
| 2006/0078929 A1 | 4/2006 | Bickel et al. |
| 2011/0160073 A1* | 6/2011 | Kordunsky ............ B01L 7/52 506/9 |
| 2016/0016171 A1 | 1/2016 | Goel |
| 2016/0230210 A1 | 8/2016 | Chen et al. |
| 2018/0156755 A1 | 6/2018 | Jeong et al. |

FOREIGN PATENT DOCUMENTS

| | | |
|---|---|---|
| KR | 10-2017-0125838 A | 11/2017 |
| KR | 10-2019-0069461 A | 6/2019 |
| KR | 10-2019-0135012 A | 12/2019 |

OTHER PUBLICATIONS

E.S. Fotso Gueutue, et al, "Nanosecond time-resolved Raman spectroscopy for solving some Raman problems such as luminescence or thermal emission", Journal of Raman Spectroscopy, 2018.

\* cited by examiner

APPARATUS AND METHOD FOR PCR DIAGNOSIS BASED ON MULTI-WAVELENGTH LIGHT SOURCE

CROSS-REFERENCE TO RELATED APPLICATIONS

This application claims priority under 35 U.S.C. § 119 to Korean Patent Application Nos. 10-2020-0107610, filed on Aug. 26, 2020, and 10-2020-0187926, filed on Dec. 30, 2020, respectively, in the Korean Intellectual Property Office, the disclosures of which are incorporated by reference herein in their entireties.

BACKGROUND

Embodiments of the present disclosure described herein relate to a diagnosis apparatus, and more particularly, relate to an apparatus and a method for a PCR diagnosis, based on a multi-wavelength light source.

Molecular diagnostic technology is a technology that analyzes molecules that cause diseases in a body, such as diseases caused by viruses, other genetic diseases, etc. Molecular diagnostic technology may analyze very accurately whether disease-causing DNA is contained through amplification of a DNA. Molecular diagnostic technology involves a process of extracting the DNA by pre-processing a bio-sample to be measured, and a process of replicating and amplifying a desired part of the extracted DNA by using a Polymerase Chain Reaction (PCR). After attaching a phosphor (e.g., SYBR green) to the amplified DNA, an intensity of the emitted fluorescent signal is measured by using an optical method. When there is emission of fluorescence corresponding to the attached phosphor, it is determined that the sample contains the DNA that causes disease.

As more the DNA is amplified, more phosphors may be attached and the intensity of fluorescence may increase. In the case of general PCR, the amplification process takes 30 cycles, and $2^{30}$ DNA chains are replicated. Using conventional PCR, it takes about 4 hours to prepare the bio-sample and to proceed with 30 cycles of amplification. It is also possible to detect multiple DNAs in one sample at once. For this, it is common to configure two or more phosphors and use a multi-wavelength light source. The multi-wavelength light source used in conventional PCR is continuous light (e.g., white light).

However, when using continuous light to detect multiple DNAs at once, as signals generated by not only a plurality of phosphors but also a phosphor not attached to the DNA chain are mixed, noise occurs. In addition, as time passes, a fluorescence intensity for continuous light of the phosphor decreases (photo bleaching). Accordingly, there is a need for a technology capable of accurately and efficiently detecting the signals generated from the phosphor while minimizing the PCR amplification cycle.

SUMMARY

Embodiments of the present disclosure provide an apparatus and a method for the PCR diagnosis that may minimize a DNA amplification cycle and improve an accuracy of detection to analyze a plurality of DNAs simultaneously.

According to an embodiment of the present disclosure, an apparatus for a polymerase chain reaction (PCR) diagnosis includes a transmitter that includes a multi-wavelength light source outputting a first light source signal and a second light source signal, which have different wavelengths, and that applies the first light source signal and the second light source signal to a DNA sample, a code generator that generates a first code signal and a second code signal corresponding to the first light source signal and the second light source signal, respectively, a delay controller that generates a first delay signal and a second delay signal corresponding to the first code signal and the second code signal, respectively, and a receiver that compares the first and second fluorescent signals emitted from the DNA sample with the first and second delay signals, and accumulatively integrates the first fluorescent signal or the second fluorescent signal based on the comparison result, and the first fluorescent signal is emitted from the DNA sample in response to the first light source signal, and the second fluorescent signal is emitted from the DNA sample in response to the second light source signal.

According to an embodiment of the present disclosure, a method for a polymerase chain reaction (PCR) diagnosis includes generating a plurality of code signals, applying a plurality of light source signals having different wavelengths to a DNA sample at different times, based on the plurality of code signals, generating a plurality of delay signals respectively corresponding to the plurality of code signals, comparing a fluorescent signal emitted from the DNA sample and the plurality of delay signals, and accumulatively integrating the fluorescent signal, based on the comparison result.

BRIEF DESCRIPTION OF THE FIGURES

The above and other objects and features of the present disclosure will become apparent by describing in detail embodiments thereof with reference to the accompanying drawings.

DETAILED DESCRIPTION

Hereinafter, embodiments of the present disclosure will be described clearly and in detail such that those skilled in the art may easily carry out the present disclosure.

Components described with reference to terms such as parts or units, modules, blocks, and ~er or ~or, which are used in the detailed description and functional blocks illustrated in the drawings may be implemented in the form of software, hardware, or a combination of hardware and software. Illustratively, the software may be machine code, firmware, embedded code, or application software. For example, the hardware may include electrical circuits, electronic circuits, processors, computers, integrated circuits, integrated circuit cores, pressure sensors, inertial sensors, microelectromechanical systems (MEMS), passive elements, or combinations thereof.

Figure 1:
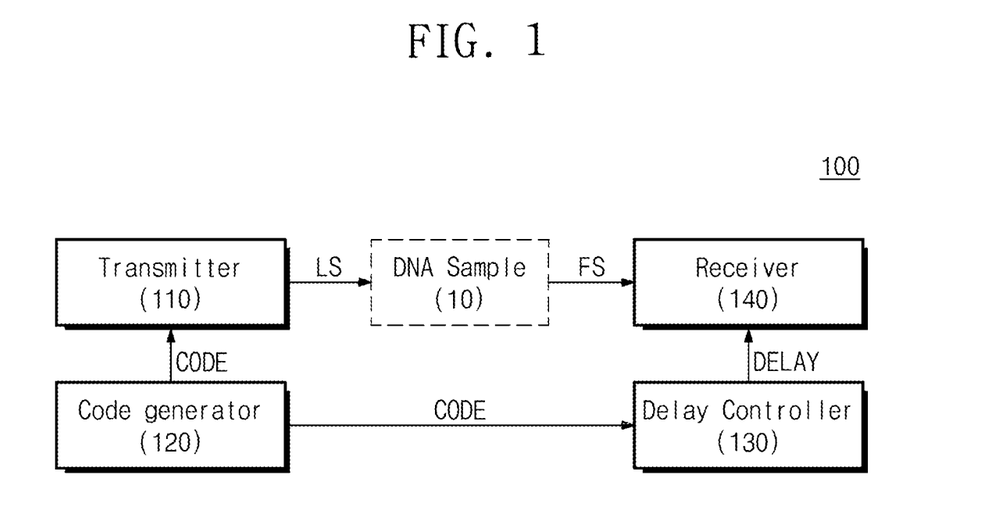
FIG. 1 is a diagram illustrating an apparatus for a PCR diagnosis according to an embodiment of the present disclosure.

FIG. 1 illustrates an apparatus 100 for a PCR diagnosis according to an embodiment of the present disclosure. The apparatus 100 may apply a light source signal LS to a DNA sample 10 including a plurality of DNAs to which a phosphor is attached. The phosphor attached to each of the DNAs of the DNA sample 10 may emit a fluorescent signal FS in response to the input light source signal LS. The apparatus 100 may receive the fluorescent signal FS emitted from the DNA sample 10 and may detect a DNA to be analyzed. The apparatus 100 may include a transmitter 110, a code generator 120, a delay controller 130, and a receiver 140.

The transmitter 110 may include a plurality of multi-wavelength light sources for applying to the DNA sample 10. For example, each of the plurality of light sources may be one of a laser diode (LD) and a light emitting diode (LED) having a limited wavelength. Hereinafter, for clear description, it is assumed that the plurality of light sources of the present disclosure are the LDs, but the present disclosure is not limited thereto. In addition, hereinafter, the light source of the present disclosure refers to a multi-wavelength light source. The number of light sources may be the same as the number of different phosphors attached to the plurality of DNAs of the DNA sample 10.

Signals output from the plurality of light sources of the transmitter 110 may be modulated based on a code signal CODE received from the code generator 120. The transmitter 110 may include at least one of a circuit, software, and firmware, which modulate the signals output from the plurality of light sources, based on the code signal CODE.

For example, a level of the signals output from the plurality of light sources may be the same as an original level while a level of the code signal CODE maintains a logic high value, and may be modulated to be zero while the level of the code signal CODE maintains a logic low value. For example, the signals output from the plurality of light sources may be modulated by a pulse amplitude modulation (PAM) method, based on the code signal CODE.

The transmitter 110 may include a plurality of optical fiber bundles for applying the modulated light source signals LS to the DNA sample 10. Each light source signal LS having a different wavelength may be transmitted through a corresponding optical fiber bundle, and may be combined in one output optical fiber by using a wavelength division multiplexing (WDM). The output optical fiber may include a splitter at its end, and each light source signal LS having the different wavelength may be applied to the plurality of DNAs through the splitter.

The code generator 120 may generate the code signal CODE for modulating signals output from the plurality of light sources of the transmitter 110. For example, the code signal CODE may be a pulse signal having the logic high value or the logic low value. The code generator 120 may apply the code signal CODE to each light source having the different wavelength to modulate signals output from the light sources.

In detail, the level of the modulated light source signal LS is the same as a level of the signal originally output from the light source while the level of the corresponding code signal CODE is maintained at the logic high value, and may be "0" while the level of the corresponding code signal CODE is maintained at the logic low value. In other words, each modulated light source signal LS may be applied to the DNA sample 10 while the level of the code signal CODE is maintained at the logic high value.

For example, the time during which the level of the code signal CODE is maintained at the logic high value may be equal to a length of a predetermined reference time. For example, the length of the predetermined reference time may be equal to or longer than a lifetime of the phosphor attached to the DNA to be applied. In addition, the time at which the signal level starts to rise from the logic low value to the logic high value may be different for each code signal CODE applied to each light source having a different wavelength.

As a result, each light source signal LS having the different wavelength may be temporally dispersed and applied to the DNA sample 10. Furthermore, the code generator 120 may transmit the generated code signal CODE to the delay controller 130. The code signal CODE will be described in more detail with reference to FIG. 2.

Different phosphors may be attached to each of the plurality of DNAs of the DNA sample 10. Different phosphors may absorb the light source signals LS having the different wavelengths, respectively. The phosphor attached to each DNA absorbs the associated light source signal LS and may emit the fluorescent signal FS. For example, the phosphor may be a cyber green (SYBR green) phosphor that absorbs a light source having a wavelength of 530 nm or less and emits a fluorescent signal having a wavelength of 550 nm or more.

Accordingly, the phosphor attached to each DNA of the present disclosure may absorb the light source signal LS having the different wavelength at different times determined based on the code signal CODE, and may emit the fluorescent signal FS corresponding to the wavelength of the absorbed light source signal LS. The fluorescent signals FS emitted from each phosphor may be provided to the receiver 140.

The delay controller 130 may receive the code signal CODE generated by the code generator 120 and may generate a delay signal DELAY corresponding to the code signal CODE. For example, the delay signal DELAY may be a signal in which the code signal CODE is delayed by a reference time. The delay controller 130 may transmit the delay signal DELAY to the receiver 140.

The receiver 140 may receive the fluorescent signals FS emitted from the phosphor attached to each DNA of the DNA sample 10. The receiver 140 may include the plurality of optical fiber bundles to receive the fluorescent signal FS. A detection array (e.g., a silicon detection array) for converting the fluorescent signal FS into an electrical signal may be positioned at ends of the plurality of optical fiber bundles. Thus, the fluorescent signal FS provided from the DNA sample 10 may be converted into the electrical signal in the detection array through the plurality of optical fiber bundles. Also, the receiver 140 may receive the delay signal DELAY from the delay controller 130.

The receiver 140 may perform a correlation integral on the fluorescent signal FS and the delay signal DELAY. First, the receiver 140 may calculate a correlation function between the fluorescent signal FS and the delay signal DELAY. By calculating the correlation function between the fluorescent signal FS and the delay signal DELAY, the receiver 140 may determine whether a coding of the input fluorescent signal FS and a coding of the delay signal DELAY are identical (that is, whether the fluorescent signal FS and the delay signal DELAY correspond to the same code signal CODE).

Next, when the coding of the input fluorescent signal FS and the coding of the delay signal DELAY are identical, the receiver 140 may accumulatively integrate the fluorescent signal FS with respect to time slots in which the level of the delay signal DELAY is maintained at the logic high value. Accordingly, while the level of the delay signal DELAY is maintained at the logic high value, the level of the corresponding fluorescent signal FS may be accumulated. The receiver 140 may include at least one of a circuit, software, or firmware, which calculate the correlation function between the fluorescent signal FS and the delay signal DELAY, and accumulatively integrate the fluorescent signal FS.

Since the fluorescent signal FS is accumulatively integrated, a gain may increase, and a DNA replication cycle may be minimized. In addition, since the delay signal DELAY is a signal in which the code signal CODE is delayed by a determined reference time, the signal obtained by accumulatively integrating the fluorescent signal FS may be a signal from which the light source signal LS applied to the corresponding phosphor is removed. Accordingly, the receiver 140 of the present disclosure may not include a filter for separately removing the light source signal LS applied to the phosphor, and a signal-to-noise ratio (SNR) may be improved.

Figure 2:
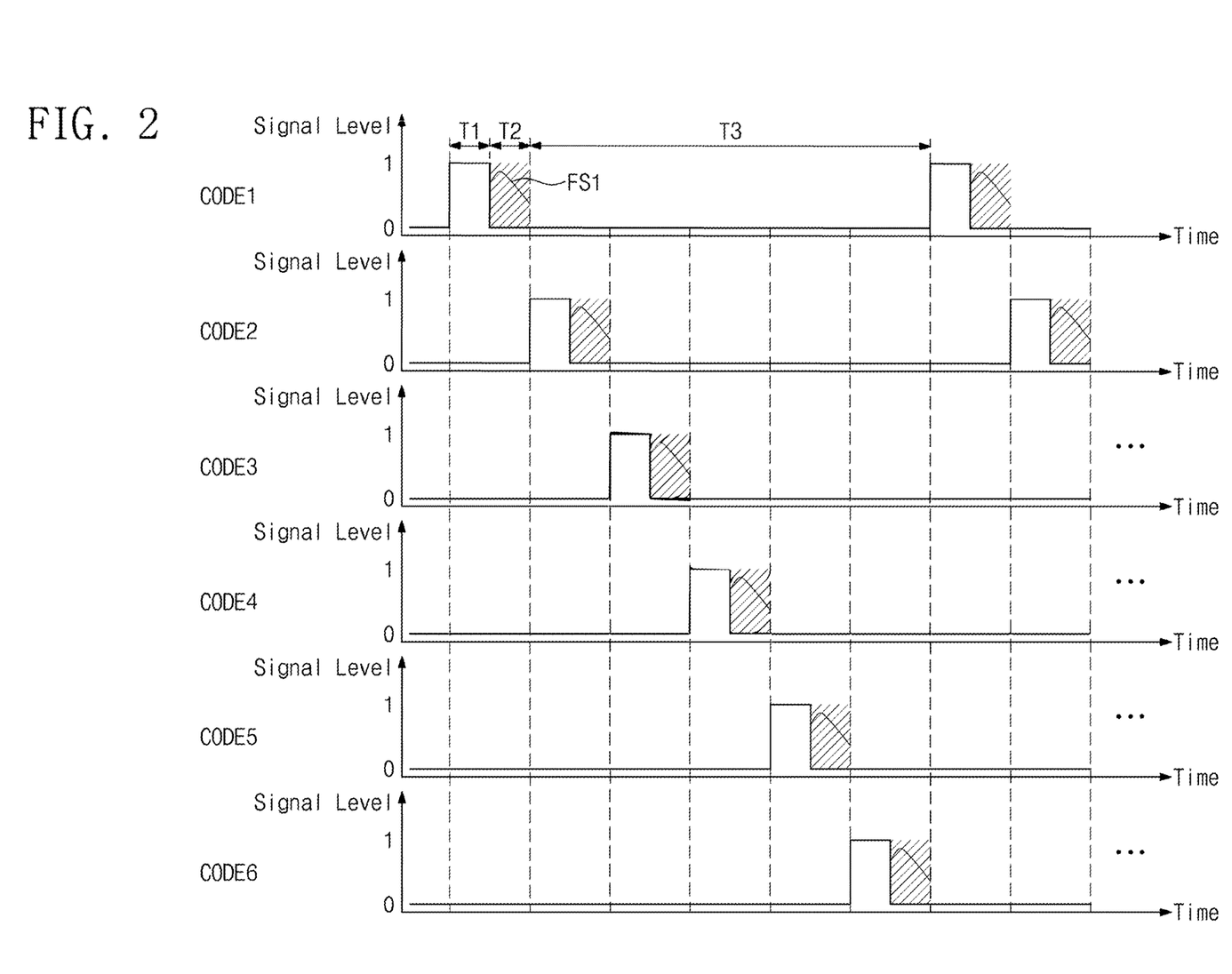
FIG. 2 is a diagram illustrating an example of a code signal generated by the code generator of FIG. 1.

FIG. 2 illustrates an example of a code signal generated by the code generator 120 of FIG. 1. As described with reference to FIG. 1, the code signal CODE of the present disclosure may be a pulse signal having the logic high value (indicated as "1" in FIG. 2) or the logic low value (indicated as "0" in FIG. 2). In FIG. 2, a horizontal axis may represent a time, and a vertical axis may represent a signal level. It will be described below with reference to FIG. 1 together with FIG. 2.

For clarity, it is assumed that the transmitter 110 includes six light sources LD1 to LD6 having different wavelengths, and the six light sources LD1 to LD6 output first to sixth light source signals LS1 to LS6, respectively. In addition, it is assumed that the code generator 120 generates six code signals CODE1 to CODE6 respectively corresponding to the six light source signals LS1 to LS6. However, the present disclosure is not limited thereto, and the number of light sources or the number of code signals may vary.

For convenience of description, the first code signal CODE1 will be described as an example. The first code signal CODE1 may be divided into three time slots T1 to T3. The first time slot T1 is a time slot in which the signal level is the logic high ("1") value, and a length of the first time slot T1 may be determined depending on the length of the reference time described with reference to FIG. 1. The first code signal CODE1 is applied to the first light source LD1 such that the first light source signal LS1 is applied to the corresponding phosphor attached to the DNA during the first time slot T1.

As described with reference to FIG. 1, the length of the reference time during which a signal level is maintained at the logic high ("1") value may be equal to or longer than the fluorescence lifetime of the phosphor corresponding to the first light source signal LS1. Also, a time slot in which the signal level is the logic high ("1") value may not be continued for a time longer than the reference time. Accordingly, after the signal level of the first code signal CODE1 is maintained at the logic high ("1") value during the reference time, a time slot in which the signal level is the logic low ("0") value may follow. During the first time slot T1, the signal level of the second to sixth code signals CODE2 to CODE6 may be maintained at the logic low ("0") value. Accordingly, only the first light source signal LS1 may be applied to the DNA sample 10, and the second to sixth light source signals LS2 to LS6 may not be applied to the DNA sample 10.

As illustrated in FIG. 2, the second time slot T2 is a time slot in which the signal level is the logic low ("0") value, and a length of the second time slot T2 is equal to the length (i.e., the length of the reference time) of the first time slot T1. In response to the first light source signal LS1 applied during the first time slot T1, the phosphor attached to the DNA during the second time slot T2 may emit the first fluorescent signal FS1. A part of the first fluorescent signal FS1 is illustrated in a shaded area of FIG. 2.

Further, the first delay signal (not illustrated) output from the delay controller 130, based on the first code signal CODE1 has a signal level of logic high ("1") in the second time slot T2. In the second time slot T2, the first delay signal and the first fluorescent signal FS1 may be compared by the receiver 140 (for example, a correlation function may be calculated), and the first fluorescent signal FS1 may be accumulatively integrated.

Since the third time slot T3 is a time slot in which the signal level of any one of the second to sixth code signals CODE2 to CODE6 is maintained at the logic high ("1") value, the signal level of the first code signal CODE1 may be maintained at the logic low ("0") value such that the first light source signal LS1 is not applied to the DNA sample 10. Changes in the signal level of the second to sixth code signals CODE2 to CODE6 over time are also the same as described for the first code signal CODE1.

Figure 3:
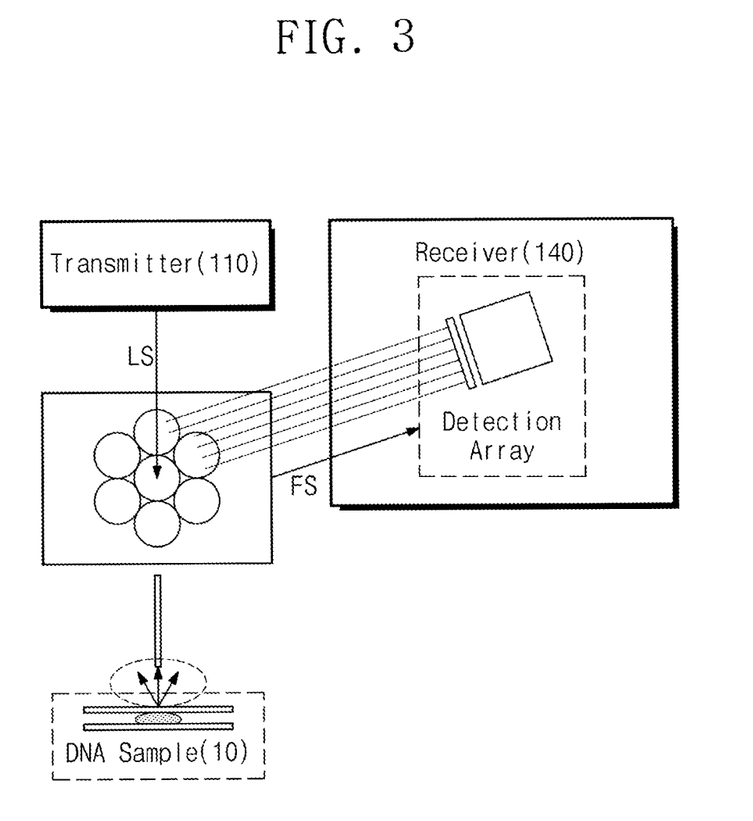
FIG. 3 is a diagram illustrating a structure of an optical fiber included in an apparatus of FIG. 1.

However, the present disclosure is not limited to the above, and the code signal generated by the code generator 120 allows the light source signals having different wavelengths to be applied at different times, but the code signal may be a pulse signal in which the logic high ("1") value and the logic low ("0") value alternately appear, unlike the first to sixth code signals CODE1 to CODE6 illustrated in FIG. 2, FIG. 3 illustrates a structure of an optical fiber included in the apparatus 100 of FIG. 1. The light source signal LS output from the light source of the transmitter 110 may be applied to the DNA sample 10 through central optical fibers of the optical fiber bundle. The fluorescent signal FS emitted from the phosphor attached to the DNA of the DNA sample 10 in response to the light source signal LS may be provided to the detection array of the receiver 140 through outer optical fibers of the optical fiber bundle, and the fluorescent signal FS may be converted into an electrical signal in the detection array.

Therefore, according to an embodiment of the present disclosure, the fluorescent signal FS of weak intensity emitted from the phosphor attached to the DNA may be transmitted through the plurality of optical fiber bundles, and thus a loss of the fluorescent signal FS may be minimized.

Figure 4:
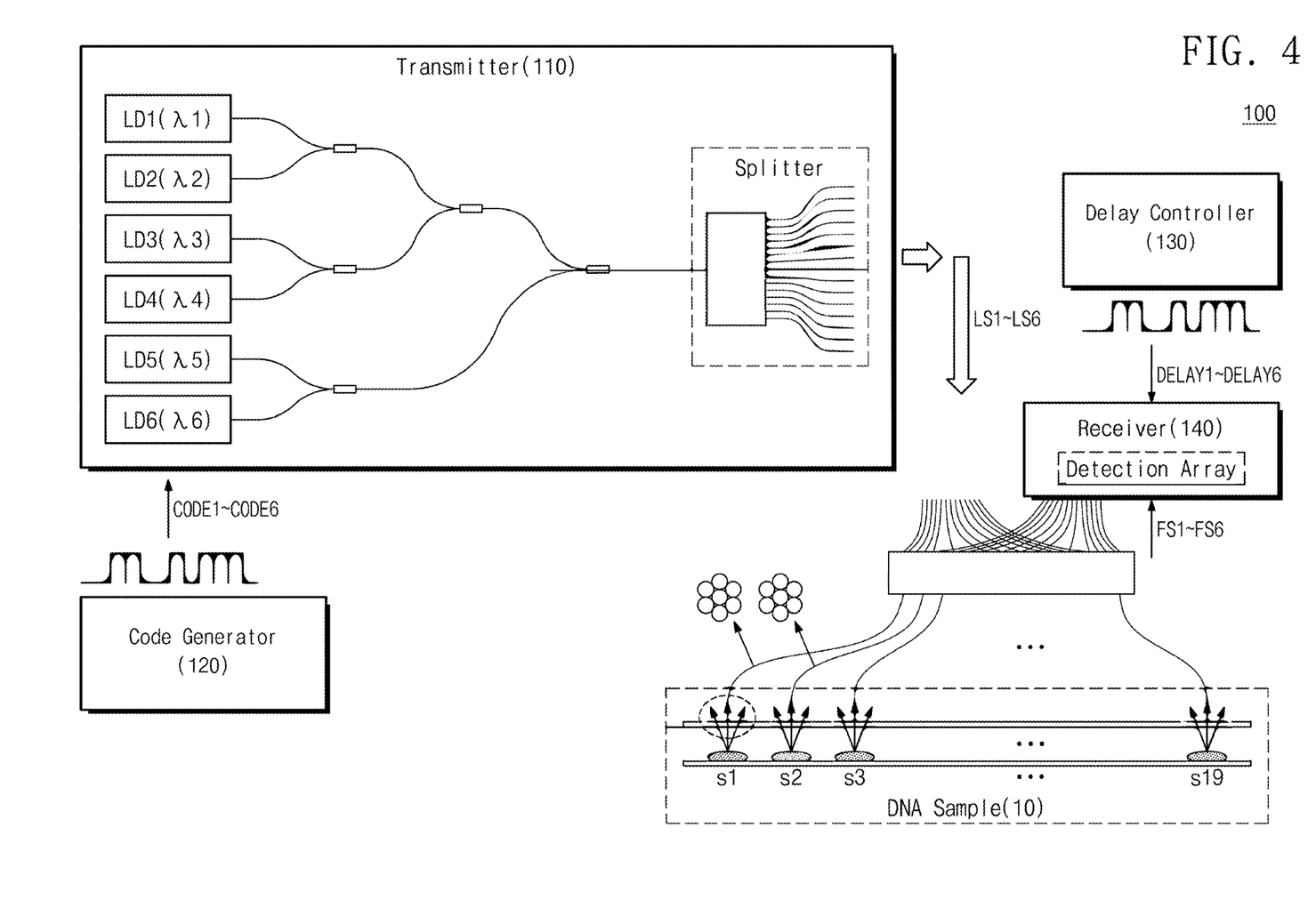
FIG. 4 is a diagram conceptually illustrating an operation of an apparatus for a PCR diagnosis according to an embodiment of the present disclosure.

FIG. 4 conceptually illustrates an operation of the apparatus 100 for PCR diagnosis according to an embodiment of the present disclosure.

The DNA sample 10 illustrated in FIG. 4 may include a plurality of DNAs s1 to s19, and a phosphor may be attached to each of the DNAs s1 to s19. The phosphor attached to each of the DNAs s1 to s19 may absorb a light source signal having a corresponding wavelength to emit a fluorescent signal. It is assumed that the number of different phosphors attached to each of the DNAs s1 to s19 of FIG. 4 is "6", and the transmitter 110 includes the first to sixth light sources LD1 to LD6 corresponding to six different phosphors, respectively. The first to sixth light sources LD1 to LD6 may have different first to sixth wavelengths $\lambda 1$ to $\lambda 6$, respectively. However, the present disclosure is not limited thereto, and the number of DNAs included in the DNA sample 10, the number of phosphors, and the number of light sources may be set differently from those illustrated in FIG. 4.

The first to sixth light sources LD1 to LD6 may be connected to the optical fiber bundles, and the first to sixth light source signals LS1 to LS6 may be output through the corresponding optical fiber bundles. The first to sixth light source signals LS1 to LS6 may be modulated by the first to sixth code signals CODE1 to CODE6 output from the code generator 120 as described with reference to FIGS. 1 and 2.

As described with reference to FIG. 1, the first to sixth light source signals LS1 to LS6 may be combined in one output optical fiber by using the wavelength division multiplexing (WDM). The output optical fiber may include a splitter at its end, and the first to sixth light source signals LS1 to LS6 having different wavelengths λ1 to λ6 may be applied to the plurality of DNAs s1 to s19 through the splitter at different times.

The phosphors attached to the plurality of DNAs s1 to s19 may receive the first to sixth light source signals LS1 to LS6 through the plurality of optical fiber bundles at different times, respectively, and may emit the corresponding first to sixth fluorescent signals FS1 to FS6. The first to sixth fluorescent signals FS1 to FS6 emitted from the DNA sample 10 may be converted into electrical signals in the detection array of the receiver 140 through the plurality of optical fiber bundles. In addition, the delay controller 130 may generate the first to sixth delay signals DELAY1 to DELAY6, based on the first to sixth code signals CODE1 to CODE6, and may transmit them to the receiver 140.

The receiver 140 may compare the first to sixth fluorescent signals FS1 to FS6 with the corresponding first to sixth delay signals DELAY1 to DELAY6, and accumulatively integrate each of the fluorescent signals FS1 to FS6. Accordingly, the device 100 may detect the plurality of DNAs s1 to s19.

Figure 5:
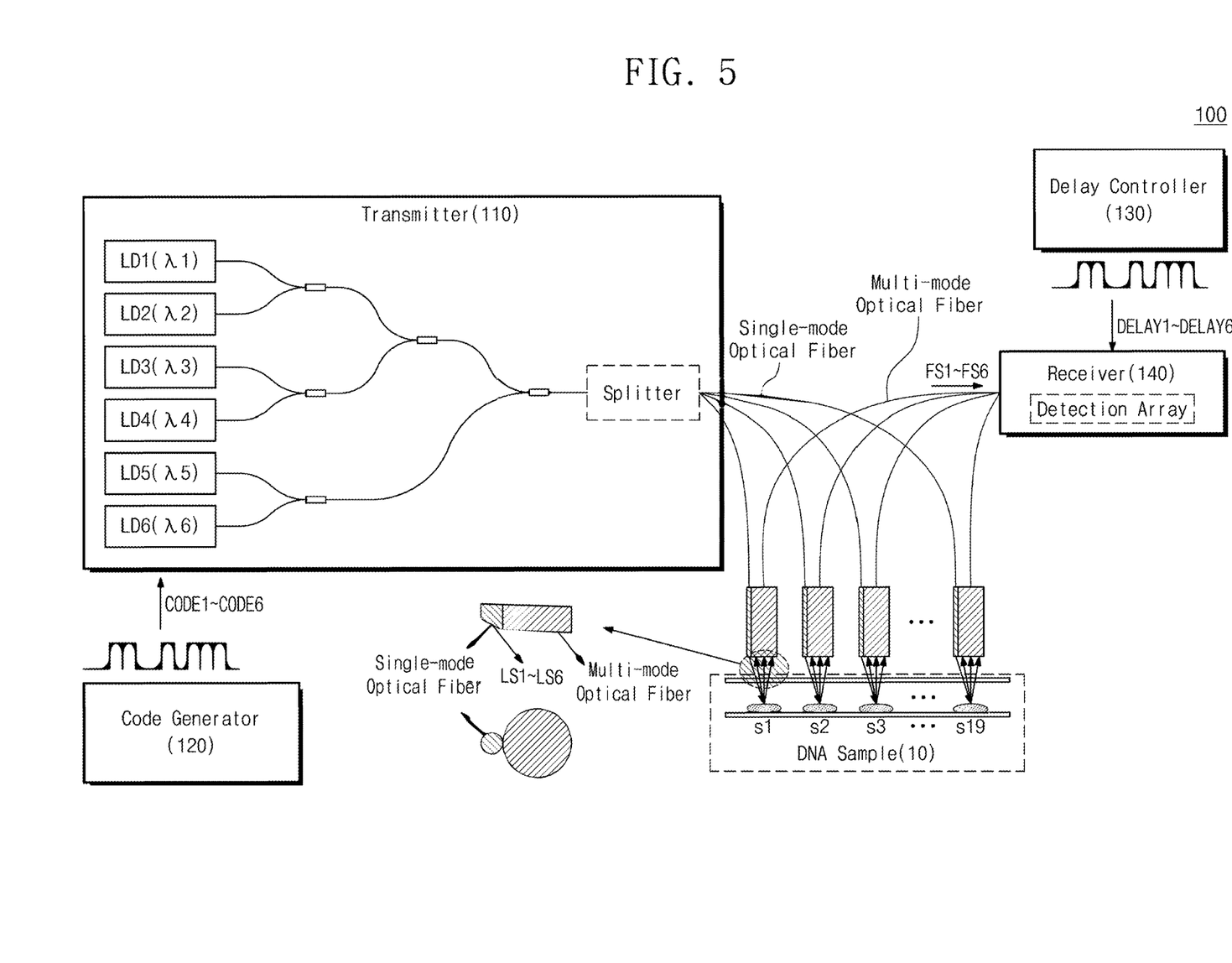
FIG. 5 is a diagram conceptually illustrating an operation of an apparatus for a PCR diagnosis according to another embodiment of the present disclosure.

FIG. 5 conceptually illustrates an operation of the apparatus 100 for PCR diagnosis according to another embodiment of the present disclosure.

While it is illustrated in FIG. 4 that the first to sixth light source signals LS1 to LS6 are provided to the DNA sample 10 through the plurality of optical fibers bundles, and the first to sixth fluorescent signals FS1 to FS6 are provided to the receiver 140 through the plurality of optical fibers bundles, in FIG. 5, it is illustrated that the first to sixth light source signals LS1 to LS6 are provided to the DNA sample 10 through a single-mode optical fiber having a small size, and the first to sixth fluorescent signals FS1 to FS6 are provided to the receiver 140 through a multi-mode fiber having a large size. Hereinafter, descriptions redundantly with FIG. 4 will be omitted.

As illustrated in FIG. 5, the single-mode optical fiber and the multi-mode optical fiber may be attached to each other. The ends of the single-mode optical fiber are inclined at an arbitrary angle to provide the first to sixth light source signals LS1 to LS6 to a center part of the DNA sample 10. Accordingly, the incident first to sixth light source signals LS1 to LS6 may be bent and may be applied to the center part of the DNA sample 10. The first to sixth fluorescent signals FS1 to FS6 may be received through the multi-mode optical fiber, and may be provided to the detection array of the receiver 140 to be converted into the electrical signal.

According to an embodiment of the present disclosure, a problem in that the fluorescence intensity of the phosphor for continuous light decreases over time may be improved.

In addition, according to an embodiment of the present disclosure, detection accuracy of PCR diagnosis may be improved by detecting only desired fluorescence without a separate fluorescence filter.

While the present disclosure has been described with reference to embodiments thereof, it will be apparent to those of ordinary skill in the art that various changes and modifications may be made thereto without departing from the spirit and scope of the present disclosure as set forth in the following claims.

What is claimed is:

1. An apparatus for a polymerase chain reaction (PCR) diagnosis comprising:
a transmitter including a multi-wavelength light source, the multi-wavelength light source outputting a plurality of light source signals that include a first light source signal and a second light source signal, wherein the first and second light source signals have different wavelengths and are respectively applied to different phosphors attached to a DNA sample;
a code generator configured to generate a first code signal and a second code signal that modulate the first light source signal and the second light source signal, respectively;
a delay controller configured to generate a first delay signal and a second delay signal based on the first code signal and the second code signal, respectively;
a receiver configured to receive the first and second delay signals from the delay controller and first and second fluorescent signals emitted from the different phosphors attached to the DNA sample, compare the first and the second fluorescent signals with the first and the second delay signals, respectively, and accumulatively integrate each of the first fluorescent signal and the second fluorescent signal based on the comparison result; and
a plurality of optical fibers configured to convey modulated signals of the first light source signal and the second light source signal to the DNA sample and transmit the first fluorescent signal and the second fluorescent signal to the receiver,
wherein the first fluorescent signal is emitted from the DNA sample in response to the modulated signal of the first light source signal, and the second fluorescent signal is emitted from the DNA sample in response to the modulated signal of the second light source signal.

2. The apparatus of claim 1, wherein the first light source signal and the second light source signal are applied to the DNA sample at different times determined based on the first code signal and the second code signal, respectively.

3. The apparatus of claim 1, wherein each of the first code signal and the second code signal is composed of a first time slot having a logic high value, a second time slot having a logic low value, and a third time slot having the logic low value, and wherein the first time slot does not appear consecutively, and the first time slot and the second time slot have a same length,
wherein the first light source signal and the second light source signal are applied to the different phosphors attached to the DNA sample during the first time slot of the first code signal and the second code signal, respectively.

4. The apparatus of claim 3,
wherein a length of the first time slot of the first code signal is equal to or longer than a fluorescence lifetime of the phosphor emitting the first fluorescent signal, and a length of the first time slot of the second code signal is equal to or longer than a fluorescence lifetime of the phosphor emitting the second fluorescent signal.

5. The apparatus of claim 3, wherein a time slot in which the first code signal has the logic high value and a time slot in which the second code signal has the logic high value are different from each other.

6. The apparatus of claim 1, wherein the first delay signal and the second delay signal are signals delayed by a time when a level of the first code signal and a level of the second code signal have a logic high value, compared to the first code signal and the second code signal, respectively.

7. The apparatus of claim 1, wherein the receiver calculates a correlation function between the first fluorescent signal and the first delay signal and a correlation function between the second fluorescent signal and the second delay signal, and accumulatively integrates each of the first fluorescent signal and the second fluorescent signal, based on a value of the calculated correlation function.

8. The apparatus of claim 1, wherein the plurality of optical fibers comprises a plurality of optical fiber bundles, and
wherein each of the modulated signals of the first light source signal and the second light source signal is applied to the DNA sample through a central optical fiber of a corresponding optical fiber bundle among the plurality of optical fiber bundles, and each of the first fluorescent signal and the second fluorescent signal is provided to the receiver through outer optical fibers of the corresponding optical fiber bundle.

9. The apparatus of claim 1, wherein the plurality of optical fibers comprises a plurality of single mode optical fibers and a plurality of multimode optical fibers, and
wherein each of the modulated signals of the first light source signal and the second light source signal is applied to the DNA sample through a single mode optical fiber, and each of the first fluorescent signal and the second fluorescent signal is provided to the receiver through a multimode optical fiber.

10. The apparatus of claim 9, wherein the single mode optical fiber is inclined at a predetermined angle such that the modulated signals of the first light source signal and the second light source signal are applied to a center part of the DNA sample.

* * * * *